United States Patent
Bammer et al.

(10) Patent No.: US 10,058,248 B2
(45) Date of Patent: Aug. 28, 2018

(54) APPARATUS FOR OBTAINING HIGH-QUALITY OPTICAL IMAGES IN A MAGNETIC RESONANCE IMAGING SYSTEM

(71) Applicant: The Board of Trustees of the Leland Stanford Junior University, Palo Alto, CA (US)

(72) Inventors: Roland Bammer, Palo Alto, CA (US); Murat Aksoy, Menlo Park, CA (US); Julian Maclaren, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/022,338

(22) PCT Filed: Sep. 17, 2014

(86) PCT No.: PCT/US2014/056077
§ 371 (c)(1),
(2) Date: Mar. 16, 2016

(87) PCT Pub. No.: WO2015/042138
PCT Pub. Date: Mar. 26, 2015

(65) Prior Publication Data
US 2016/0228005 A1   Aug. 11, 2016

Related U.S. Application Data
(60) Provisional application No. 61/878,969, filed on Sep. 17, 2013.

(51) Int. Cl.
*A61B 5/055*   (2006.01)
*A61B 5/00*    (2006.01)
(Continued)

(52) U.S. Cl.
CPC ............ *A61B 5/0035* (2013.01); *A61B 3/112* (2013.01); *A61B 3/113* (2013.01); *A61B 5/0013* (2013.01);
(Continued)

(58) Field of Classification Search
CPC ...... A61B 2090/306; A61B 2090/3937; A61B 2562/0233; A61B 3/112; A61B 3/113;
(Continued)

(56) References Cited

U.S. PATENT DOCUMENTS 7,173,426 B1 *  2/2007  Bulumulla ......... G01R 33/3692
                                                      324/318
7,988,688 B2    8/2011  Webb
(Continued)

FOREIGN PATENT DOCUMENTS

JP  2005-512704     5/2005
JP  2007-144192     6/2007
WO  WO2013074578    5/2013

*Primary Examiner* — Mark Remaly
(74) *Attorney, Agent, or Firm* — Lumen Patent Firm

(57) ABSTRACT

A miniature, low-power, optical sensing device that operates in the harsh electromagnetic environment of a magnetic resonance imaging system is provided. The device includes a means of transferring imaging data obtained with the optical sensor out of this harsh electromagnetic environment without requiring a galvanic connection. It is practical to power the device using a small battery that is compatible with the harsh environment. In other embodiments, the device is powered using 'power over fiber' or by taking power by 'power harvesting' directly from the harsh electromagnetic environment. One embodiment is to directly integrate the device into a magnetic resonance imaging (MRI) head coil, using a wired connection to the head coil to provide electrical power. Here the wired connection does
(Continued)

not penetrate the Faraday cage of the MRI system or cross into the bore of the MRI system from outside the bore.

12 Claims, 4 Drawing Sheets

(51) Int. Cl.
| | |
|---|---|
| *G01R 33/28* | (2006.01) |
| *A61B 3/11* | (2006.01) |
| *A61B 3/113* | (2006.01) |
| *A61B 5/0205* | (2006.01) |
| *G01R 33/48* | (2006.01) |
| *G01R 33/565* | (2006.01) |
| *G01R 33/34* | (2006.01) |
| *A61B 90/30* | (2016.01) |
| *A61B 90/00* | (2016.01) |
| *A61B 5/024* | (2006.01) |
| *A61B 5/08* | (2006.01) |

(52) U.S. Cl.
CPC .......... *A61B 5/0059* (2013.01); *A61B 5/0077* (2013.01); *A61B 5/02055* (2013.01); *A61B 5/055* (2013.01); *A61B 5/721* (2013.01); *G01R 33/283* (2013.01); *G01R 33/4808* (2013.01); *G01R 33/56509* (2013.01); *A61B 5/02416* (2013.01); *A61B 5/08* (2013.01); *A61B 2090/306* (2016.02); *A61B 2090/3937* (2016.02); *A61B 2562/0233* (2013.01); *G01R 33/34046* (2013.01)

(58) Field of Classification Search
CPC ... A61B 5/0013; A61B 5/0035; A61B 5/0059; A61B 5/0077; A61B 5/02055; A61B 5/02416; A61B 5/055; A61B 5/08; A61B 5/721; G01R 33/283; G01R 33/34046; G01R 33/4808; G01R 33/56509
See application file for complete search history.

(56) References Cited

U.S. PATENT DOCUMENTS

| | | |
|---|---|---|
| 8,121,361 B2 | 2/2012 | Ernst |
| 8,214,012 B2 | 7/2012 | Zuccolotto |
| 2007/0049794 A1* | 3/2007 | Glassenberg ...... A61B 1/00032 600/109 |
| 2009/0187112 A1* | 7/2009 | Meir ..................... A61B 5/113 600/534 |
| 2009/0209846 A1 | 8/2009 | Bammer |
| 2010/0245543 A1 | 9/2010 | Greer |
| 2010/0312097 A1 | 12/2010 | Gallant |
| 2011/0201916 A1 | 8/2011 | Duyn |
| 2011/0230755 A1 | 9/2011 | MacFarlane |
| 2012/0121124 A1 | 5/2012 | Bammer |
| 2012/0253178 A1 | 10/2012 | Mostafavi |
| 2012/0323113 A1 | 12/2012 | Biber |
| 2013/0053683 A1 | 2/2013 | Hwang |
| 2014/0046167 A1 | 2/2014 | Vij |

* cited by examiner

APPARATUS FOR OBTAINING HIGH-QUALITY OPTICAL IMAGES IN A MAGNETIC RESONANCE IMAGING SYSTEM

STATEMENT OF GOVERNMENT SPONSORED SUPPORT

This invention was made with Government support under contract EB011654 awarded by the National Institutes of Health. The Government has certain rights in the invention.

FIELD OF THE INVENTION

The present invention relates to medical imaging. Specifically, it involves a device for obtaining high quality optical data from a human or animal subject during simultaneous magnetic resonance imaging.

BACKGROUND

Magnetic resonance imaging (MRI) is an invaluable tool in clinical imaging. MRI uses a strong static magnetic field ($B_0$), a powerful radio-frequency (RF) field ($B_1$), and rapidly switching magnetic field gradients to generate and spatially encode signals. Due to these magnetic fields, patient monitoring during the MRI procedure can be challenging, as it is difficult to operate electronics in this environment. The static fields used are often between 1.5 T and 7 T, which precludes the use of ferromagnetic materials in any electronic device placed inside the scanner bore. The RF field is a source of electromagnetic interference and the gradient fields are a source of mechanical vibrations and eddy currents in conductive materials. Not only must any electronic monitoring device be capable of operating in this environment, but it should not perturb the MRI fields in any way, as this can result in artifacts in the MR images.

Despite these challenges, it is advantageous to be able to optically monitor the head or body of the patient during the MRI procedure. One major area of application is the correction of motion. MRI is extremely sensitive to motion. Head movements of only a few millimeters during a typical 5-10 minute scan produce severe image artifacts, often rendering the images useless. This can affect the outcome for the patient and increases costs if scans must be repeated. One promising motion correction method involves measuring the head pose (position and orientation) of the subject using optical camera systems. Video information is used to track a marker mounted on the head of the subject. Head motion data are then used for real-time control of the scanner. This involves updating the RF and gradient fields of the scanner to compensate for the motion of the head, thereby ensuring that there is no relative motion between the imaging volume and the object. This technique is very powerful, as it is applicable to all common imaging sequences.

Motion correction has motivated several recent developments in patient monitoring for MRI. One existing approach involves placing cameras outside the scanner away from the strongest magnetic fields (U.S. Pat. No. 8,121,361). This has the major disadvantage that an unimpeded line of sight to the tracking marker attached to the subject is required. Another implementation involves placing cameras inside the bore of the MRI scanner, either directly attached to the bore or mounted on the head coil used to receive RF signal (US 2009/0209846 and US 2011/0201916). This helps achieve clear line of sight, although parts of the head coil can still obscure the view of any optical marker used. To circumvent the problem of obscured view to an optical marker, a self-encoded marker can be used that allows determination of which part of the marker is seen by the camera (US 2012/0121124). Furthermore, the need to provide power to the apparatus via a conductive cable can cause electromagnetic interference with the MRI procedure. Finally, existing implementations require cameras to be manually positioned and calibrated by the scanner operator, in some cases prior to every scan. These issues have been a barrier to the adoption of the technique as a routine clinical tool because they interfere with workflow.

In addition to motion correction, there are many other uses for high-quality video information from the subject during the MRI procedure. Eye tracking is often used in functional MRI (fMRI) experiments; patient skin temperature could be measured by thermal mapping leveraging the thermal sensitivity (e.g. infrared) of an optical detector; physiological signals, such as pulse rate and oxygen saturation, could be detected from slight color changes in the skin; respiratory signals could be measured from optical motion data without requiring the use of a pneumatic respiratory belt. It would therefore be an advance in the art to provide an optical imaging system that (a) ensures unimpeded line of sight to the subject (b) is completely MR compatible and (c) requires minimal user interaction to setup and maintain.

SUMMARY

This work provides methods for obtaining high-quality video data of a subject during simultaneous magnetic resonance imaging. The present approach avoids the problems mentioned earlier; namely, poor line of sight to the subject, interference with the MRI scanner, and excessive user interaction.

The apparatus comprises one or more miniature cameras, which are modified to be MR compatible and then preferably embedded into the imaging coil of the MRI scanner. This ensures unimpeded view of the subject or of any tracking marker attached to the subject. Additionally, the operator does not need to install the camera prior to use, as it is an integral part of the MRI system. Unlike existing implementations, the miniature camera has no galvanic connection to the outside world, which improves its robustness to strong static and switching magnetic fields and ensures that it does not electromagnetically perturb its environment.

In a preferred embodiment, both control of the camera and transfer of image data are achieved optically using a digital signal. To allow practical operation, a low power mechanism for image data transfer is used. In this embodiment, this is achieved optically using a low-power optical link. The preferred cable used is an 'active optical cable', where there is no optical connector, but rather miniature (largest dimension <3 mm) electrical connectors attached to each end of the optical cable. In this embodiment, two fibers are used, where one is used to transmit control signals to the camera from outside the MRI room and the other is used to receive image data. In one embodiment, the two fibers are fused together to form a single 'cable' and they share an electrical connector. In this embodiment, each electrical connector contains a VCSEL (vertical-cavity surface-emitting laser) and a low-power VCSEL driver chip to convert electrical signals into optical signals, as well as a photodiode and transimpedance amplifier to produce a voltage from the optical signal. In this embodiment, the fibers are polymer optical fibers, but glass optical fibers may also be used.

In another embodiment, closely related to the above-described embodiment, data communication is performed using 'optical USB' cables. Typically, optical USB cables also contain copper wire in order to transport power. In this embodiment, the copper is removed and power is supplied to the electronic components independently at each end of the cable. In a similar way, optical Thunderbolt® or optical HDMI can be used.

In another embodiment, data communication is performed wirelessly at a frequency above that used by the MRI scanner, to avoid interference with the MR imaging process. This can be done by using gigabit Wi-Fi (IEEE 802.11ac) or WiGig (IEEE 802.11ad), which can achieve sufficient data rates to transfer video streams with low power consumption.

The use of a low power data transfer mechanism and camera chip ensures that the power required by the unit, including LED lighting, is less than 500 mW. This enables the device to be powered without requiring a copper power cable. In the preferred embodiment, there is no galvanic connection from the device to the outside world, because the apparatus is powered using MR-compatible batteries, such as rechargeable lithium polymer cells, which can be manufactured without the use of nickel, or other ferromagnetic material. The battery contacts are made of copper, which has attractive MR-compatibility properties. Each battery is very small, such that it fits within the RF shield of the apparatus. Battery life can be several hours or greater.

In a preferred embodiment, the battery is sealed inside a copper-shielded case. The case slides on to the main camera unit and forms an electrical connection using a two-pin connector. In this way, the battery can be easily removed for charging and a fresh battery can be installed in its place. This can be done without moving the camera out of its place (e.g. no removal of the camera from the MR head coil is needed for the case of a camera integrated with the MR head coil).

In another embodiment, the apparatus is powered using 'power over fiber', where light from a laser diode or LED located outside the scanner room is directed along an optical fiber to the apparatus. The light is then converted back into electrical energy using a photovoltaic cell.

In a further embodiment, the apparatus is powered using a connection to the scanner receive coil. In this embodiment, current is drawn from the receive coil power supply to power the optical imaging apparatus without any effect of the performance of the receive coil. To achieve this, filters, including passive electronic components, may be required in some cases.

In a further embodiment, the apparatus is powered via a "power harvesting" scheme, where the switching of the magnetic gradient field can induce voltage in a pickup coil to power the system or via the time-varying RF field itself.

A further advantage of these approaches is that the low-power components have very low heat dissipation, which helps the device maintain a constant temperature. This prevents drifts in the data output that would otherwise result from device heating.

DETAILED DESCRIPTION

Figure 1:
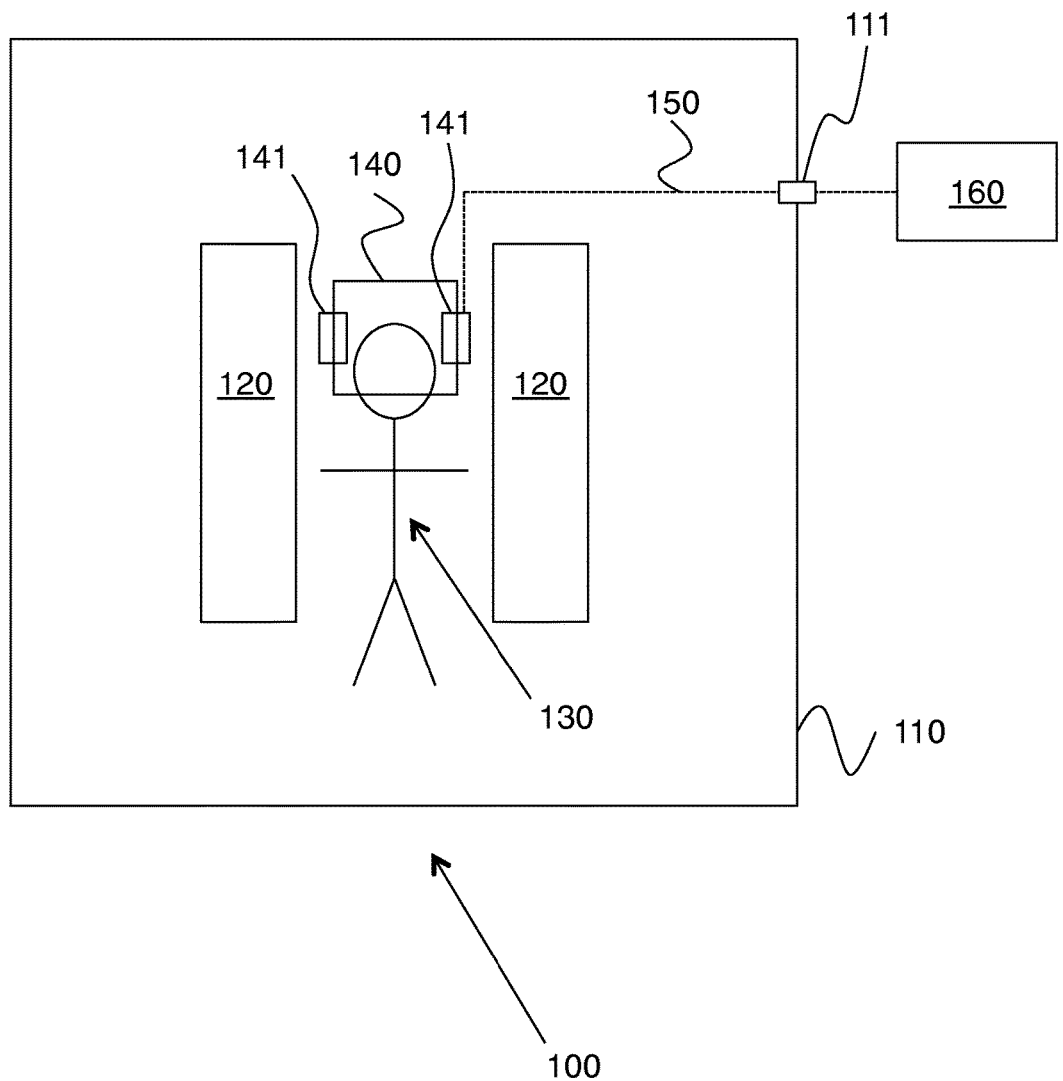
FIG. 1 shows an example of camera integration into an MRI scanner and Faraday cage.

FIG. 1 shows an exemplary apparatus according to the above-described principles. Apparatus 100 includes a Faraday cage 110, which encloses a magnetic resonance imager 120, in which a human (or animal) 130 is placed. The head of the human, or animal, is partially enclosed by an imaging coil 140, which includes one or more integrated cameras 141. The only data communication with camera(s) 141 is via optical fibers 150, which pass through the Faraday cage via a waveguide 111 to a processing device 160.

Figure 2A:
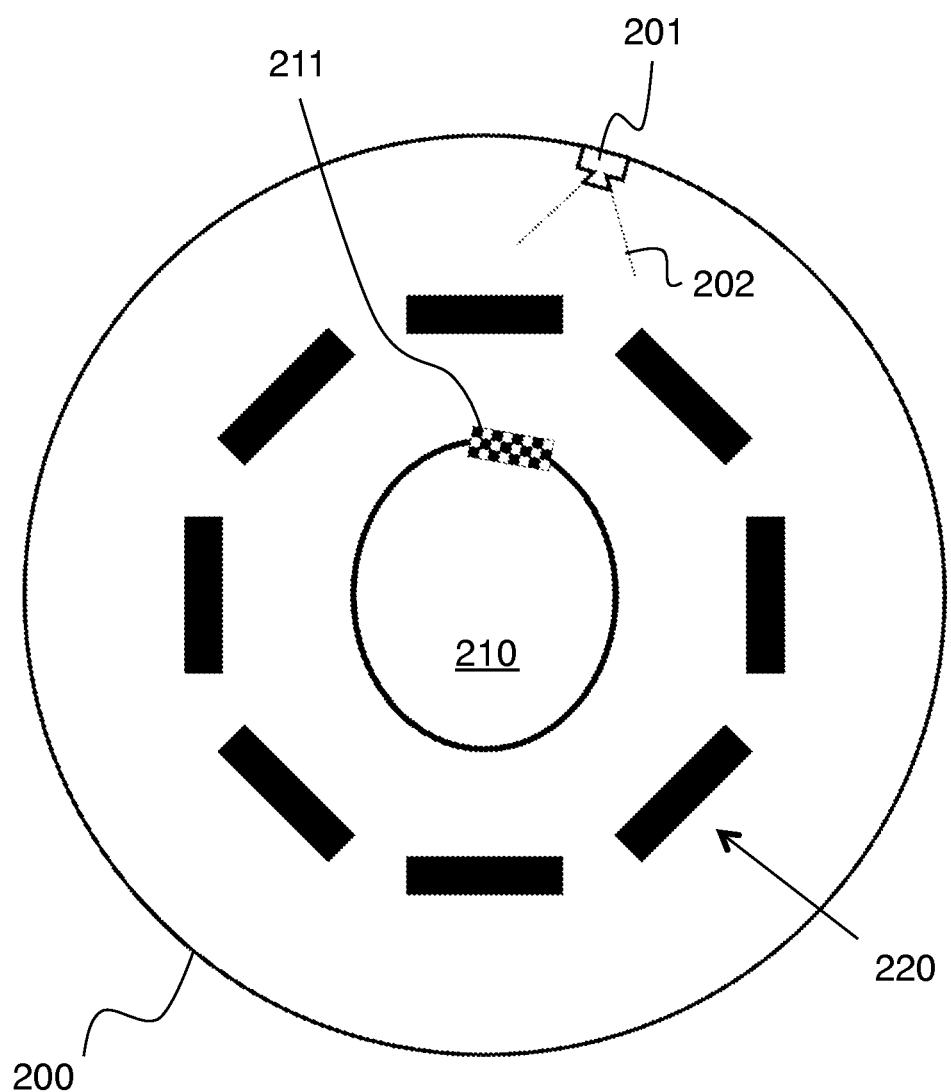
FIG. 2A shows an exemplary bore-mounted camera arrangement.

To better appreciate the present invention, it is helpful to consider the drawbacks of bore-mounted cameras. FIG. 2A shows an MRI scanner bore 200 that surrounds a patient's head 210 with attached tracking marker 211. As can be seen in this figure, a bore mounted camera 201 will suffer from the disadvantage that its field of view 202 will be significantly blocked by head coil 220.

Figure 2B:
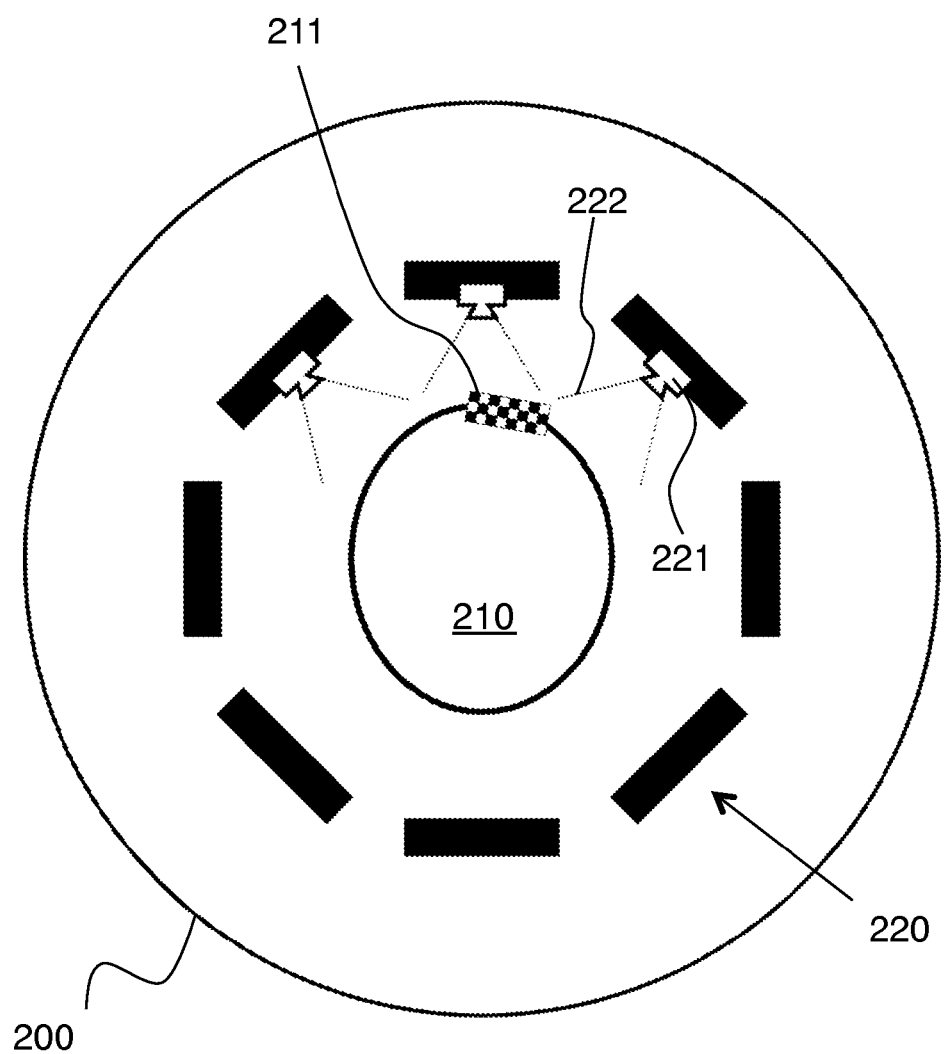
FIG. 2B shows an exemplary head coil mounted camera arrangement.

FIG. 2B shows a similar arrangement, except that cameras 221 are mounted on (or preferably integrated with) head coil 220, thereby providing an improved field of view 222 for observing target 211. This improved field of view is why the configuration of FIG. 2B is preferred relative to the configuration of FIG. 2A. Preferably tracking marker 211 has a position self-encoding pattern on it, as described in US 2012/0121124, hereby incorporated by reference in its entirety.

Figure 3:
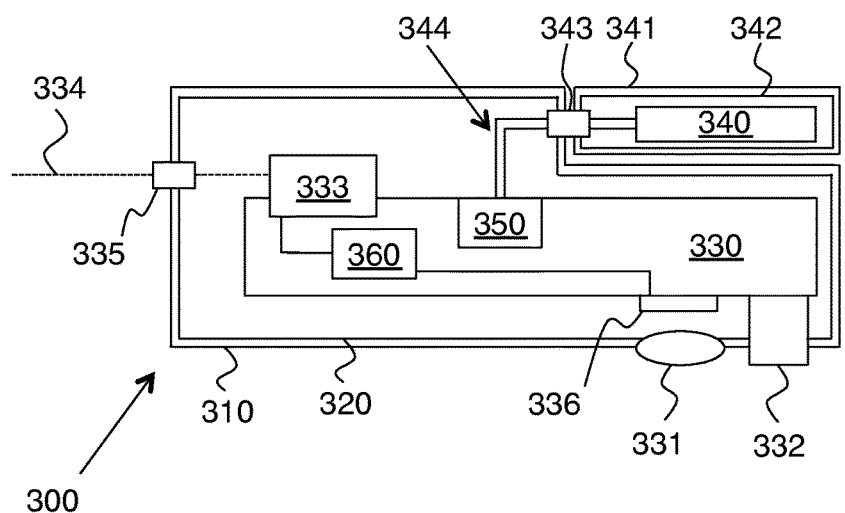
FIG. 3 shows an example of a camera module with no wired connection into the bore of the MRI system.

FIG. 3 shows an example camera module 300, encased in a plastic enclosure 310 lined with a conductive shield 320. The conductive shield 320 can be made of copper foil and/or copper paint. The module preferably includes a single printed circuit board 330, which includes a camera 336, lens 331, an LED 332 (to provide illumination when required) and an active optical fiber connector 333, so that all data to and from the camera can be transferred using one or more optical fibers 334. The entire unit can be powered using a rechargeable MR-compatible lithium polymer battery 340, where all contacts that would typically be nickel plated have been replaced with copper.

For example, an on-board power electrical supply 350 can receive energy from battery 340. Alternatively, as described above, on-board power supply 350 can receive electrical power from any other source, as long as no wired connection into the bore of the MRI system is made. The on-board power supply 350 can be anything that receives electrical power from outside the circuit board. For example, a connector and optionally a voltage regulator may suffice for power supply 350, depending on details of the power configuration employed.

The battery is also encased in a plastic enclosure 341 lined with a conductive shield 342. Power from the battery is transferred to the camera unit using a connector 343 and local wire connections 344. Control of camera 336 is via controller 360, which also has no wired connection into the bore of the MRI system. In this example, inputs to controller 360 are provided via optical fiber(s) 334. Note that in this embodiment, the conductive shields of the camera case and battery (320 and 342 respectively) are entirely isolated and have no galvanic connection to ground, the MRI scanner, the battery or any components on the PCB. This configuration has outstanding MR compatibility properties.

Figure 4:
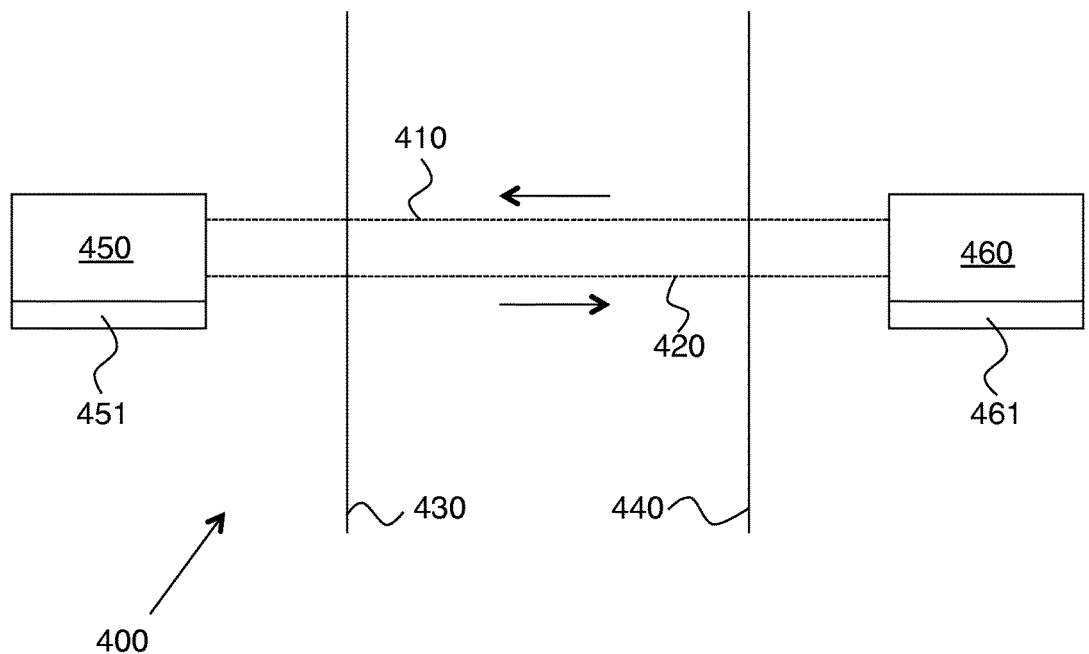
FIG. 4 shows a schematic of a preferred data transfer approach.

FIG. 4 shows a preferred data transfer system 400. Two plastic optical fibers 410 and 420 are fused together to form a bi-directional optical cable. One of the fibers 410 is used to transfer data relating to camera control (e.g. exposure time, image matrix, frame rate, etc.). The other fiber 420 is used to transfer the image data from the camera to a computer. These fibers are the only physical connection that runs out of the camera shielding 430 and the Faraday cage 440 of the MRI scanner room. The advantage of this setup is that no electrical signals are present, which results in excellent electromagnetic compatibility with the MRI system. The two-fiber cable is an 'active optical cable', meaning that there are connectors 450 and 460 attached to the fiber at each end. Both connectors preferably have length, width and height of less than 3 mm. To convert electrical signals to optical signals, each connector contains a VCSEL and a low-power VCSEL driver chip. To convert optical signals to electrical signals, each connector includes a photodiode and a transimpedance amplifier. The connector 450 inside the camera case has electrical contacts 451, which are connected to the camera electronics. The connector 460 outside the Faraday cage has electrical contacts 461, which are connected to a computer (e.g., via a USB interface). This communication system allows image data from the camera to be received by the computer and also allows camera settings such as exposure time and gain to be controlled from the computer.

The preceding examples describe an optical sensing apparatus for use in an electromagnetic (EM) environment provided by a magnetic resonance imaging (MRI) system, where the apparatus includes:
1) one or more EM-compatible optical sensors (e.g., 336);
2) one or more electrical power sources (350) for the optical sensors, where power is provided to the electrical power sources via power connections that have no wired connection into the bore of the MRI system;
3) one or more controllers (360) for the optical sensors, where input commands are provided to the controllers via control connections that have no wired connection into the bore of the MRI system; and
4) one or more sensor output units (160), where output signals from the optical sensors are provided to the sensor output units via output connections that have no wired connection into the bore of the MRI system. Here a wired connection is defined to be any connection that makes use of a conductive material (e.g., a metal) to conduct electricity. Thus an optical fiber is not a wired connection because there is no conduction of electricity. In other words, at any point where the power, control and/or output connections cross into the bore of the MRI system, these connections are non-wired (e.g., optical fiber, wireless link, etc.). Wired connections can be used in cases where the wiring is entirely within the bore of the MRI system, such as providing power via a wired connection to a local battery or via a wired connection to an MRI head coil. Wired connections can also be used within parts of the camera system that are completely outside the bore of the MRI system.

The optical sensing apparatus is preferably disposed on or in a head coil of the MRI system. In these cases, the power connections preferably include a wired connection to the head coil. In cases where a tracking marker is disposed on a subject being imaged, the optical sensing apparatus preferably has a field of view that includes part or all of the tracking marker. The one or more EM-compatible optical sensors can be configured as a detector array in complementary metal-oxide semiconductor (CMOS) or charge-coupled device (CCD) technology.

The control connections can be via optical fiber or wireless link. Similarly, the output connections can also be via optical fiber or wireless link. In cases where optical fiber is used for these connections, one or more bidirectional optical fiber links including one or more optical fibers can be used. Such bidirectional optical fiber links can include vertical cavity surface emitting lasers as optical sources.

Suitable power connections include but are not limited to: wired connections to a local battery, wired connections to the MRI system, wired connections to a head coil of the MRI system, optical fibers, wireless links, and power harvesting from the EM environment. In all of these cases, no wired connection into the bore of the MRI system from outside the bore of the MRI system is made, thereby preserving the above-described MR compatibility.

In operation, the above-described apparatus can be used to optically observe a subject during MR imaging. For example, pulse monitoring, breathing monitoring, tracking eye movement, monitoring pupil size, and monitoring skin temperature are some applications. Recognizing movements of the subject being imaged and operating instrumentation based on the recognized movements can also be done.

An application of particular significance is performing motion tracking and motion correction to mitigate motion-induced artifacts based on the output signals from the optical sensors. Such motion tracking can include any or all of the following methods: using markers for motion tracking, using natural features of the subject for motion tracking, and projecting a pattern of light onto the subject for motion tracking.

The invention claimed is:

1. An optical sensing apparatus for use in an electromagnetic (EM) environment provided by a magnetic resonance imaging (MRI) system, the apparatus comprising:
    one or more EM-compatible optical sensors, wherein the optical sensors are disposed on or in a head coil of the MRI system;
    one or more electrical power sources for the optical sensors;
    a wired connection between the electrical power sources and the head coil of the MRI system;
    wherein power is provided to the electrical power sources by the head coil via the wired connection;
    one or more controllers for the optical sensors;
    fiber optic control connections from outside a bore of the MRI system to the one or more controllers for the optical sensors inside the bore of the MRI system;
    wherein input commands are provided to the controllers via the fiber optic control connections; and
    one or more sensor output units;
    fiber optic output connections from the optical sensors inside the bore of the MRI system to the sensor output units outside the bore of the MRI system;
    wherein output signals from the optical sensors are provided to the sensor output units via the fiber optic output connections.

2. The apparatus of claim 1, further comprising a tracking marker disposed on a subject being imaged, wherein the optical sensing apparatus has a field of view that includes part or all of the tracking marker.

3. The apparatus of claim 1, wherein the one or more EM-compatible optical sensors are configured as a detector array in complementary metal-oxide semiconductor (CMOS) or charge-coupled device (CCD) technology.

4. The apparatus of claim 1, further comprising an illumination source.

5. The apparatus of claim 4, wherein the illumination is configured to provide a pattern of light onto a subject being imaged, wherein the pattern of light is visible to the one or more EM-compatible optical sensors.

6. The apparatus of claim 1, wherein the control connections and the output connections are provided by one or more bidirectional optical fiber links including one or more optical fibers.

7. The apparatus of claim 6, wherein the bidirectional optical fiber links include vertical cavity surface emitting lasers as optical sources.

8. A method of magnetic resonance imaging (MRI) comprising:
   i) providing an optical sensing apparatus for use in an electromagnetic (EM) environment provided by an MRI system, the apparatus comprising:
   one or more EM-compatible optical sensors, wherein the optical sensors are disposed on or in a head coil of the MRI system;
   one or more electrical power sources for the optical sensors;
   a wired connection between the electrical power sources and the head coil of the MRI system;
   wherein power is provided to the electrical power sources by the head coil via the wired connection;
   one or more controllers for the optical sensors;
   fiber optic control connections from outside a bore of the MRI system to the one or more controllers for the optical sensors inside the bore of the MRI system;
   wherein input commands are provided to the controllers via the fiber optic control connections; and
   one or more sensor output units;
   fiber optic output connections from the optical sensors inside the bore of the MRI system to the sensor output units outside the bore of the MRI system;
   wherein output signals from the optical sensors are provided to the sensor output units via the fiber optic output connections; and
   ii) using the optical sensing apparatus for optically observing a subject during MRI.

9. The method of claim 8, wherein observing the subject being imaged comprises one or more methods selected from the group consisting of: pulse monitoring, breathing monitoring, tracking eye movement, monitoring pupil size, and monitoring skin temperature.

10. The method of claim 8, further comprising recognizing movements of the subject being imaged and operating instrumentation based on the recognized movements.

11. The method of claim 8, further comprising performing motion tracking and motion correction to mitigate motion-induced artifacts based on the output signals from the optical sensors.

12. The method of claim 11, wherein the motion tracking comprises one or more methods selected from the group consisting of: using markers for motion tracking, using natural features of the subject for motion tracking, and projecting a pattern of light onto the subject for motion tracking.

* * * * *